US010705079B2

(12) United States Patent
Rao et al.

(10) Patent No.: US 10,705,079 B2
(45) Date of Patent: Jul. 7, 2020

(54) METHOD FOR PREPARING MAGNETIC MICROSPHERE FOR SEPARATION OF BIOLOGICAL PROTEIN AND USE THEREOF

(71) Applicant: SHENZHEN NEW INDUSTRIES BIOMEDICAL ENGINEERING CO., LTD., Shenzhen, Guangdong (CN)

(72) Inventors: Wei Rao, Guangdong (CN); Kai Du, Guangdong (CN); Li Zhao, Guangdong (CN)

(73) Assignee: SHENZHEN NEW INDUSTRIES BIOMEDICAL ENGINEERING CO., LTD., Shenzhen (CN)

( * ) Notice: Subject to any disclaimer, the term of this patent is extended or adjusted under 35 U.S.C. 154(b) by 80 days.

(21) Appl. No.: 15/126,816

(22) PCT Filed: May 29, 2014

(86) PCT No.: PCT/CN2014/078840
§ 371 (c)(1),
(2) Date: Sep. 16, 2016

(87) PCT Pub. No.: WO2015/180110
PCT Pub. Date: Dec. 3, 2015

(65) Prior Publication Data
US 2017/0089890 A1  Mar. 30, 2017

(51) Int. Cl.
*G01N 33/543* (2006.01)
*C08F 220/14* (2006.01)
*C08F 220/28* (2006.01)
*C08L 33/12* (2006.01)
*G01N 33/53* (2006.01)
*C08F 222/14* (2006.01)
*G01N 33/577* (2006.01)

(52) U.S. Cl.
CPC ....... *G01N 33/5434* (2013.01); *C08F 220/14* (2013.01); *C08F 220/28* (2013.01); *C08F 222/14* (2013.01); *C08L 33/12* (2013.01); *G01N 33/53* (2013.01); *G01N 33/54326* (2013.01); *G01N 33/54393* (2013.01); *G01N 33/577* (2013.01); *C08F 220/281* (2020.02); *G01N 33/54333* (2013.01)

(58) Field of Classification Search
CPC .... C08F 220/14; C08F 222/14; C08F 220/28; C08F 2220/281; C08L 33/12; G01N 33/53; G01N 33/577; G01N 33/54393; G01N 33/5434; G01N 33/54326; G01N 33/54333
See application file for complete search history.

(56) References Cited

U.S. PATENT DOCUMENTS 5,736,349 A * 4/1998 Sasaki ............... B03C 1/01
435/7.94

2005/0014001 A1  1/2005 Fonnum et al.
2013/0303703 A1  11/2013 Wei et al.

FOREIGN PATENT DOCUMENTS

| CN | 1070509 A | 3/1993 |
| CN | 101220187 A | 7/2008 |
| CN | 101241130 A | 8/2008 |
| CN | 102746529 A | 10/2012 |
| CN | 104031201 A | 9/2014 |
| EP | 0201211 A1 | 11/1986 |
| EP | 2000484 A1 | 12/2008 |
| JP | 10270233 A | 10/1998 |
| JP | 2008191128 A | 8/2008 |
| WO | WO 2009/028449 A1 | 3/2009 |

OTHER PUBLICATIONS

Bayramuglu et al. Covalent immobilization of chloroperoxidase onto magnetic beads: catalytic properties and stability. Biochemical Engineering Journal 2008, vol. 38, pp. 180-188. (Year: 2008).*
Du et al. Synthesis of hemispherical poly(2-hydroxyethyl methacrylate-co-methyl methacrylate)/Poly(styrene-co-glycidyl methacrylate) composite particles with heterobifunctional groups by soap-free seeded emulsion polymerization. Macromolecules 2004, vol. 37, pp. 803-812. (Year: 2004).*
Gao et al. Rapid magnetic solid-phase extraction based on magnetite/silica/poly(methacrylic acid-co-ethylene glycol dimethacrylate) composite microspheres for the determination of sulfonamide in milk samples. J. Chromatography 2010, vol. 1217, pp. 5602-5609. (Year: 2010).*
"Novel Biological Samples Pretreatment Based on Restricted Access Magnetic Microspheres," pp. 1-122, (2011).
"Preparation of Magnetic Composite Microspheres by Template Mini-emulsion Polymerization and Their Application in Protein Purification", pp. I-X and 1-141 (2008).
"Synthesis and characterization of polymethyl methacrylate magnetic microspheres", Chunli Liu and Shanshan Li, Journal of Nanyang Institute of Technology, vol. 4, No. 4, pp. 127-128 (2012).
Extended European search report dated Oct. 5, 2017, issued by European Patent Office.

(Continued)

*Primary Examiner* — Shafiqul Hao
(74) *Attorney, Agent, or Firm* — Finnegan, Henderson, Farabow, Garrett & Dunner LLP

(57) ABSTRACT

Disclosed is a method for preparing a magnetic microsphere for the separation of biological proteins. A magnetic microsphere matrix is treated by formulating and using an appropriate emulsified liquid, and modification of the surface of the magnetic microsphere matrix is realized by emulsion polymerization, thereby obtaining a magnetic microsphere coated with a polyacrylate polymer layer. Said emulsified liquid comprises the following components therein: acyclic acid monoester compounds, acyclic acid glycol compounds, initiators and optionally anionic surface active agents and water. The magnetic microsphere significantly reduces the non-specific adsorption of other proteins, without affecting the joining ability for a specific protein, when used in the separation of biological proteins. A new selection is provided to realize the separation engineering of high protein specificity adsorption.

12 Claims, No Drawings

(56) References Cited

OTHER PUBLICATIONS

Frey, Na et al., "Magnetic nanoparticles: synthesis, functionalization, and applications in bioimaging and magnetic energy storage," Chem. Soc. Rev. (2009) 38(9):2532-2542.
Thermo-Fisher Scientific Inc., Online catalog, "http://www.lifetechnologies.com/order/catalog/en/US/adirect/It?cmd=catDisplay" archived on Mar. 31, 2014.

* cited by examiner

METHOD FOR PREPARING MAGNETIC MICROSPHERE FOR SEPARATION OF BIOLOGICAL PROTEIN AND USE THEREOF

TECHNICAL FIELD

The present disclosure relates to the technical field of biological protein separation. More specifically, it refers to a method for preparing magnetic microspheres for separation of biological protein and use thereof.

BACKGROUND

Magnetic nanoparticles (such as $Fe_3O_4$ nanoparticles) have unique properties of nanomaterials, such as small particle size, large surface area, higher coupling capacity, and the like. Meanwhile, they also have magnetic responsiveness and superparamagnetism, capable of gathering and positioning in a constant magnetic field and absorbing electromagnetic waves to generate heat in an alternating magnetic field. In addition, the magnetic nanoparticles can also be subjected to surface modification with a variety of active functional groups (such as —OH, —COOH, —$NH_3$, etc.). Thus, the magnetic nanoparticles have broad application prospects in the biomedical fields for, for example, such as bio-separation, drug delivery, hyperthermia therapy for cancer, and the like, and have received extensive attention.

In biological and medical fields, a magnetic microsphere usually refers to a magnetic polymer microsphere, which is a magnetic material developed in recent years, typically manufactured by forming magnetic composite microspheres by combining magnetic inorganic particles (such as $Fe_3O_4$) with organic polymer materials. Prior magnetic microspheres can be provided with a variety of functional groups on their surfaces by means of surface modification or the like and therefore have been widely applied in the fields of biology, cytology, separation engineering, and the like. Particularly, the magnetic microspheres have outstanding advantages in biological separation and purification, immunoassays, biological testing, and similar areas, for being easy to use, fast, and efficient, among other features.

Magnetic microspheres for biological separation typically require the following properties: (1) superparamagnetism; (2) uniform particle size; (3) good dispersion in an aqueous phase; (4) low non-specific adsorption; (5) surface chemical groups available for modification. Magnetic microspheres also have significant advantages in proteins separation. For example, magnetic separation techniques can be applied in large-scale operations; the separation process may be performed directly in raw samples containing suspended solid particles or other biological particles; and, the separation process is simple and fast.

However, non-specific adsorption of proteins on the surface of magnetic microspheres is disastrous for their use in bio-separation. It will not only damage the specific separation effect by microspheres, but also increase background signal in a quarantine assay, decreasing the signal to noise ratio. A typical strategy to prevent non-specific adsorption of proteins on magnetic nanoparticles or magnetic microspheres is to perform surface chemical modification.

Patent Document CN102746529A discloses a method for preparing monodisperse magnetic microspheres by emulsion polymerization. However, the magnetic microspheres prepared by this method suffer from high non-specific adsorption of proteins, rendering a high signal-to-noise ratio in immunoassays. In addition, such method is too costly for industrial production.

Patent Document CN92105584.6 discloses a method for preparing immune magnetic microspheres by suspension polymerization. In this method, $\gamma$-$Fe_2O_3$ or $Fe_3O_4$ magnetic powders are surface-modified with long-chain fatty acids and then subjected to suspension polymerization in a styrene solution to generate the immune magnetic microspheres. Though the magnetic microspheres prepared by this method are low cost, they are high in non-specific protein adsorption yet poor in aqueous dispersibility.

Wang et al. used a porous $\gamma$-$Fe_2O_3$@ $SiO_2$ magnetic silica as the matrix. An epoxy-modification was performed first, followed by forming a diol group by opening the ring of the epoxy group on the outer surface using a polymer acid with a particle size of 50 μm, reacting the remaining epoxy groups on the inner surface with octadecylamine, sodium bisulfite, and triethylamine hydrochloride, respectively, and eventually generating a novel magnetic restricted access material with octadecyl group, sulfonic acid group, and quaternary ammonium salt group in sequence on the inner surface and with diol group on the outer surface (Wang Yu. Novel preparation technology for biological samples based on restricted access functionalization of magnetic microspheres [D], Tianjin University, 2012). The diol group on the outer surface of the material can play a role in protein exclusion, while the magnetic restricted access material with sulfonic acid group and quaternary ammonium salt group on the inner surface has a much higher adsorption volume for small molecules than a material with octadecyl group on the inner surface. However, the preparation method of magnetic microspheres disclosed in this paper is relatively complicated, while their specific separation effects for biological proteins remains disputed.

SUMMARY OF THE INVENTION

One aspect of the present disclosure is to provide a magnetic microsphere, which can be used for separation of biological proteins and significantly reduce or eliminate non-specific protein adsorption.

Another important aspect of the present disclosure is to provide a method for preparing the magnetic microspheres as described above. For this method, the Inventors have conducted extensive research and abundant tests to select the appropriate components and contents for the emulsion, combining with a magnetic matrix, so as to obtain magnetic microspheres with reduced or eliminated non-specific adsorption of other proteins without affecting the binding with specific proteins.

Furthermore, the present disclosure also provides the use of the magnetic microspheres as described above in immunoassay applications.

According to the present disclosure, there is provided a method for preparing a magnetic microsphere for separation of biological protein, comprising following steps: a. preparing an emulsion; b. dispersing a magnetic microsphere matrix with magnetism into the emulsion to generate a dispersion system; and c. subjecting the dispersion to a polymerization reaction; wherein, the magnetic microsphere matrix is a magnetic particle modified with a active group on surface thereof; and the emulsion comprises the following components: an acrylic monoester compound, an acrylic diol ester compound, and an initiator. The initiator is preferably a water-soluble initiator. The acrylic monoester compound acts as a polymeric monomer, while the acrylic diol ester compound functions as a crosslinking agent. The magnetic microsphere matrix as used in the above method can be provided with specific types of functional groups by modification. Further, under the action of the initiator, the acrylic monoesters can go through a crosslinking polymerization with the crosslinking agent to form a coating on surface of the magnetic microspheres. As a result, said magnetic microspheres are generated. Unlike the prior art, the present disclosure employs the above-described emulsion to modify the magnetic microsphere matrix not for the purpose of introducing active groups and carrying the same with polymer. Instead, the magnetic microsphere matrix is further modified, based on the active groups that are already present on the magnetic microsphere matrix, by emulsion polymerization with a specific emulsion that forms a polymer layer, so that magnetic microspheres can have reduced or eliminated non-specific adsorption of other proteins without affecting the binding ability with specific proteins (such as antigens) via the active groups. The mechanism of the present disclosure will be described below, without limiting the present disclosure in any aspect. The magnetic microspheres coated with polyacrylate polymers prepared by the method of the present disclosure have filled surface voids, depressions, and other defects (such voids, depressions, and other defects are important reasons for nonspecific adsorption of interfering antibodies with certain shape (e.g., Y-shaped)) and smoother surface, which greatly reduce the non-specific adsorption of other proteins.

In a preferred embodiment, the emulsion may further comprise an anionic surfactant and water. Acrylic monoester compounds and acrylic diol ester compounds are strongly hydrophobic while the magnetic microsphere matrix is hydrophilic. As a result, the magnetic microspheres cannot have sufficient contact with the acrylic monomers or acrylic esters diol esters. When a highly water-soluble surfactant is added, it will not only improve the dispersion of the magnetic microspheres, but also facilitate the adsorption of polymer to the surface of the magnetic microspheres for polymerization. By coating the magnetic microsphere matrix as described, some physical defects on the microsphere surface can be remedied at the same time.

In some embodiments of the present disclosure, the emulsion may comprise 0.5 to 30 wt % of the acrylic monoester compound, 0.05 to 5 wt % of the acrylic diol ester compound, 0.2 to 2 wt % of a water-soluble initiator, 0.1 to 1 wt % of a water-soluble anionic surfactant, and 62 to 99 wt % of water, based on the total weight of the emulsion. The content of the acrylic monoester compound is preferably 0.1 to 15 wt %, still preferably 2 to 10%. The content of the acrylic diol ester compound is preferably 0.1 to 2%. The content of the acrylic monoester compound is more preferably 0.5 to 20 wt % by, and even more preferably 2 to 15 wt %. Moreover, it should be understood that, the acrylic monoester compound as described above is not limited to a single compound, but can be any mixture of acrylic monoester compounds. The same applies to the other components such as the acrylic diol ester compounds. In addition, the specific types and contents of the individual compounds can not be considered in isolation but as a whole, taking into account the synergetic effects of the emulsion components and their specific contents, in order to achieve the best effect of the emulsion on the surface modification of the magnetic microsphere. For example, the acrylic diol ester compounds with a content of less than 0.05% will have poor crosslinking polymerization with monomers. Consequentially, the surface modification of the magnetic microspheres cannot be ideal to achieve the technical effect of the present disclosure of improved signal to noise ratio. On the other hand, when the content is too high, the remaining acrylic diol ester compounds may react with the active groups of the magnetic microsphere matrix, reducing the binding ability of the magnetic microspheres with the antigen proteins later on, compromising the assay results. The contents of the acrylic monoester compounds are determined with the same considerations as described above. In the present disclosure, by selecting such an emulsion formula, a polymer layer is formed on the surface of the magnetic microsphere matrix after polymerization. This polymer layer does not affect the binding ability of the magnetic microspheres with specific proteins (via the active groups), while reducing the non-specific actions of other proteins on the magnetic microspheres. Meanwhile, the stability in physicochemical properties of the magnetic microspheres is ensured. These beneficial effects can be illustrated, for example, from the following examples.

In some preferred embodiments of the present disclosure, the weight content of the acrylic diol ester compounds may be 5 to 15% of the acrylic monoester compounds, and more preferably 10%, in order to obtain a polymer layer of suitable thickness and optimize the polymerization reaction so that a synergetic effect between the crosslinking agent and monomers can be achieved without incurring any byproduct. Therefore, the binding ability for specific proteins with the active groups of the magnetic microspheres can be further ensured, while reducing the non-specific adsorption of other proteins with the magnetic microspheres.

Acrylic monoester compounds suitable for use in the present disclosure may include, but not limited to, methyl methacrylate, ethyl methacrylate, hydroxyethyl methacrylate, n-propyl methacrylate, hydroxypropyl methacrylate, n-butyl methacrylate, and hydroxybutyl methacrylate. Acrylic diol ester compounds suitable for use in the present disclosure may include, but not limited to, glycol dimethacrylate, 1,3-propanediol dimethacrylate, 1,3-butanediol dimethacrylate, 1,4-butanediol dimethacrylate, neopentyl glycol dimethacrylate, and 1,6-hexanediol dimethacrylate. Water-soluble initiators suitable for use in the present disclosure may include, but not limited to, sodium persulfate, potassium persulfate, and ammonium persulfate. Anionic surfactants suitable for use in the present disclosure may include, but not limited to, sodium dodecyl sulfate, sodium dodecyl sulfonate, sodium hexadecyl sulfonate, and sodium n-decyl sulfate. Water used in the present disclosure is preferably purified water.

In the present disclosure, in order to reduce the subsequent non-specific adsorption of other proteins by the magnetic microspheres, without affecting the subsequent ability of binding to specific proteins or affecting the physical and chemical properties (such as magnetism and dispersibility in aqueous phase) of the magnetic microspheres, crosslinking polymerization of acrylic monoester compound with acrylic diol ester compound in the emulsion is performed to eventually form a magnetic microsphere coated by a polyacrylate polymer layer on the surface of the magnetic microsphere matrix. To reduce the subsequent non-specific adsorption of other proteins by the magnetic microspheres without affecting binding to specific proteins, it is necessary to introduce active groups on the surface of the magnetic microspheres before the crosslinking polymerization of the acrylic monoester compound with the acrylic diol ester compound. The active groups can bond with a biological protein. The active groups, may be, for example, a sulfhydryl group, a hydroxyl group, a carboxyl group, an amino group, an epoxy group, an aldehyde group, an cyanate group, an isocyanate group, a cyano group, an isocyano group, an allyl group, a benzyl group, a propenyl group, a maleimide group, a N-hydroxy succinimidyl ester group, a carbonyl group, a phenolic hydroxyl group, a sulfonic acid group, an oxime group (including aldoxime, ketoxime, etc.), an azo group, a hydrazone group, and the derivative groups thereof. Magnetic microsphere matrix used in the present disclosure may be obtained by surface modification of unmodified magnetic particles according to known methods or by direct purchase. The unmodified magnetic particles may be, for example, nanoparticles of $\gamma$-$Fe_2O_3$, $MeFe_2O_3$(Me=Co, Mn, Ni), $Fe_3O_4$, Ni, Co, Fe, Fe—Co and Ni—Fe alloys, preferably nanoparticles of $\gamma$-$Fe_2O_3$ and/or $Fe_3O_4$. Suitable magnetic microsphere matrix may be available from, for example, Dynabeads (Dynal, Norwegian), Estapor microspheres (Cat. No. M1-070/60, Merck), Sera-Mag microspheres (Cat. No. 2415-2105-050250, Thermo Scientific), Dynabeads microspheres (Cat. No. M-280, LifeTechnologies), and the like.

The present disclosure may use a magnetic microsphere matrix with a preferable particle size of 0.1 to 5 μm. In this size range, the magnetic microsphere matrix may have good dispersion in an aqueous phase as well as ensuring a larger surface area. The magnetic microsphere matrix may be solid, hollow, or porous. The magnetic microsphere matrix preferably takes a spherical shape. Spherical magnetic microsphere matrix has a large surface area with optimal adsorption effect.

In the dispersion system, the magnetic microsphere matrix of excessively large concentration may prone to aggregation, while the magnetic microsphere matrix of excessively small concentration may have poor results of emulsion polymerization and low production efficiency. Accordingly, after extensive experiments, the Inventors have chosen a concentration of magnetic microsphere matrix in the dispersion system as 10 to 400 mg/mL, preferably 10 to 200 mg/mL, more preferably 10 to 150 mg/mL, and even more preferably 20 to 100 mg/mL. In this concentration range, the magnetic microsphere matrix can be uniformly and stably dispersed in a dispersion system, while providing good polymerization results.

To ensure a suitable thickness of the polyacrylate polymer layer coating the magnetic microsphere matrix and optimal effects of surface modification of the magnetic microsphere matrix, in the step c) of this method, the polymerization reaction is preferably performed at 60 to 90° C., and more preferably at 70 to 75° C. It is also preferred to perform the polymerization reaction under stirring for 10 to 40 h, and more preferably 15 to 30 h.

In one embodiment, the method of the present disclosure may further comprise a step d) after the step c): performing a solid-liquid separation with the product of the step c) and washing the solid matter obtained therefrom to generate the magnetic microspheres.

In some particular embodiments, in step a), the emulsion may be prepared by mixing together the components of the emulsion evenly, e.g., by stirring or sonication to dissolve the solid components of the emulsion, and optionally, by homogenization treatment (such as homogenization using a high-pressure homogenizer, a high-shear emulsifier, and the like), so that the components of the emulsion can mix well with each other to obtain an emulsion. In step b), the magnetic microsphere matrix may be dispersed in the emulsion by ultrasonication. In step d), the solid-liquid separation may be performed by magnetic separation or centrifugation; the washing may be performed for a plurality of times with organic solvent and water in sequence; and, the organic solvent may be one or more selected from the group consisting of alcohol (e.g., methanol, ethanol, propanol, isopropanol, butanol, etc.), ester (e.g. ethyl acetate, butyl acetate, etc.), and halogenated hydrocarbon.

The present disclosure further provides a magnetic microsphere prepared according to the method described above, comprising a magnetic microsphere matrix with magnetism and a polyacrylate compound coating the magnetic microsphere matrix. The coating of polyacrylate materials may remedy some surface defects on the magnetic microsphere matrix, thereby reducing the subsequent non-specific adsorption, without affecting the ability of binding to proteins.

In the magnetic microspheres of the present disclosure, the thickness of the polyacrylate polymer in the surface coating is particularly important. The active groups on the surface of the magnetic microsphere matrix may be blocked if the coating is too thick, which subsequently affects the ability of binding to proteins. However, if the coating is too thin, surface physical modification of the magnetic microsphere matrix cannot be successful to reduce the non-specific adsorption. The Inventors have conducted a large number of studies to obtain a magnetic microsphere on which the thickness of the polyacrylate surface coating is 0.001 to 5 μm, preferably 5 nm to 1000 nm, further preferably 10 to 500 nm, even more preferably 10 to 100 nm, and still more preferably 50 nm to 100 nm. Polyacrylate polymer layers in this thickness range advantageously do not affect the subsequent binding of the surface groups of the magnetic microspheres with specific proteins, while reducing or eliminating non-specific adsorption of magnetic microspheres with other proteins as well as avoiding affecting the physical and chemical properties, such as magnetism, of the magnetic microspheres themselves.

Furthermore, the present disclosure also provides the used of a magnetic microsphere prepared according to the method described above was used in biochemical assays, for example, in immunoassays, especially in chemiluminescence quantative immunoassay. Such applications are, for example, applications in chemiluminescence immunoassays of a variety of specific total antibodies, specific IgG class antibodies, or specific IgM class antibodies in human serum.

In some particular applications, the present disclosure provides a magnetic microsphere that may be used in a chemiluminescence quantitative immunoassay for at least one selected from the group consisting of: anti-*toxoplasma* IgG antibody, anti-*toxoplasma* IgM antibody, glutamic acid decarboxylase antibody, rubella virus IgG antibody, rubella virus IgM antibody, cytomegalovirus IgG antibody, cytomegalovirus IgM antibody, Type I/II herpes simplex virus IgG antibody, Type I/II herpes simplex virus IgM antibody, EB virus IgG antibody, and EB virus IgM antibody.

The method for preparing magnetic microspheres of the present disclosure prepares a suitable emulsion, uses the same to treat a magnetic microsphere matrix, and achieves surface modifications on the magnetic microsphere matrix by emulsion polymerization, to generate a magnetic microsphere that can be used in biological separation. When used in biological protein separation, this magnetic microsphere can significantly reduce subsequent non-specific adsorption with other proteins without compromising the binding ability to specific proteins, thereby solving a major challenge in biological protein isolation and providing a new option for achieving high specific adsorption of proteins in a separation project. The magnetic microspheres prepared by the present method have good dispersibility suitable for large-scale operation, while the separation method is relatively easy for practice. In addition, the procedure of the preparation method is also simple while the raw materials used are cheap and readily available. Therefore, it has great value in use and economic significance.

DETAILED DESCRIPTION OF EMBODIMENTS

Further description of the present disclosure will be provided below with specific embodiments. However, it should be understood that the scope of the present disclosure is not limited thereto.

Example 1

1) Preparation of Magnetic Microsphere Matrix

The magnetic microsphere matrix with carboxyl functional group used in the present example was prepared according to Example 1 of the Chinese Patent CN92105584.

2) Preparation of Emulsion

The components of the emulsion and their percentages by weight were as follows:

| | |
|---|---|
| Methyl methacrylate | 5%; |
| Ethylene glycol dimethacrylate | 0.5%; |
| Potassium persulfate | 0.3%; |
| Sodium dodecyl sulfate | 0.2%; and |
| Purified Water | 94%. |

The above components were mixed according to their proportions, sonicated to fully dissolve the solid components, and further well mixed.

3) Preparation of Dispersion System

The magnetic microsphere matrix obtained from step 1) was dispersed in the emulsion prepared from step 2) at a concentration of 20 mg/mL, and sonicated for uniform dispersion of the magnetic microsphere matrix to obtain a dispersion system.

4) Polymerization Reaction and Post-Treatment

The dispersion system obtained from step 3) was stirred at 75° C. for 30 hours. The supernatant was removed by magnetic separation. The solids were washed 3 times with methanol and 5 times with water to give the magnetic microspheres.

5) Determination of Binding Performance of Surface Active Groups of Magnetic Microspheres 5a) Choice of test samples: *toxoplasma* IgG (TOXO IgG) negative and positive samples (n=10 for each), glutamic acid decarboxylase (GAD65) negative and positive samples (n=10 for each), and cytomegalovirus IgM (CMV IgM) negative and positive samples (n=10 for each). All of the above samples were confirmed by clinical verification.

5b) Antigen-coated magnetic microspheres: The TOXO antigen, GAD65 antigen, and CMV antigen were used for coating the magnetic microspheres prepared in the present example. The coated magnetic microspheres were diluted with phosphate buffer saline (PBS) by a certain proportion to a working concentration of 0.5 mg/mL.

5c) Preparation of luminescent markers: ABEI (N-(4-aminobutyl)-N-ethyl isoluminol)-labeled monoclonal mouse anti-human IgG antibody (anti-hIgG-ABEI) (diluted with PBS to 0.02 μg/mL), ABEI-labeled staphylococcal protein A (SPA-ABEI) (diluted with PBS to 0.04 μg/mL), and ABEI-labeled mouse anti-human IgM monoclonal antibody (anti-hIgM-ABEI) (diluted with PBS to 0.02 μg/mL) were used respectively as the luminescent markers for detection of TOXO IgG, GAD65, and CMV IgM.

5d) Method for sample adding determination: *Toxoplasma* IgG antibody (TOXO IgG) assay kit, glutamic acid decarboxylase antibody (GAD65) assay kit, and cytomegalovirus IgM antibody (CMV IgM) assay kit from New Industries Biomedical Engineering Co., LTD (Shenzhen, China) were used in sample adding determination according to the corresponding kit instructions. Luminescent signal intensities were determined using MAGLUMI 2000 Plus Automated Chemiluminescence Analyzer (New Industries Biomedical Engineering Co., LTD, Shenzhen, China).

The results are shown in Table 1 to 3.

6) Non-Specific Adsorption Test of Magnetic Microspheres

6a) Choice of test samples: normal human serum with clinically verified negativity for TOXO IgG, GAD65 and CMV IgM.

6b) Preparation of luminescent markers: ABEI (N-(4-aminobutyl)-N-ethyl isoluminol)-labeled monoclonal mouse anti-human IgG antibody (anti-hIgG-ABEI) (1:4000 diluted with PBS), ABEI-labeled staphylococcal protein A (SPA-ABEI) (1:3000 diluted with PBS), and ABEI-labeled mouse anti-human monoclonal IgM antibody (anti-hIgM-ABEI) (1:4000 diluted with PBS) were used as luminescent markers for detecting TOXO IgG, GAD65, and CMV IgM.

6c) Antigen-coated magnetic microspheres: The TOXO antigen, GAD65 antigen, and CMV antigen were used for coating the magnetic microspheres of the present example. The coated magnetic microspheres were diluted with phosphate buffer saline (PBS) by a certain proportion to a working concentration of 0.5 mg/mL.

6d) Method for sample adding determination: *Toxoplasma* IgG antibody (TOXO IgG) assay kit, glutamic acid decarboxylase antibody (GAD65) assay kit, and cytomegalovirus IgM antibody (CMV IgM) assay kit from New Industries Biomedical Engineering Co., LTD (Shenzhen, China) were used in sample adding determination according to the corresponding kit instructions. The results are shown in Table 4.

Comparative Example 1

The magnetic microsphere matrix was prepared according to the method disclosed in the Chinese Patent CN92105584, and tested for the binding performance and non-specific adsorption of their surface active groups. The tests were performed in similar process and conditions according to the steps 5) and 6) of Example 1, except that the magnetic microsphere matrix used in the steps 5) and 6) of Example 1 were replaced with the magnetic microspheres prepared in the present comparative example. The results are shown in Table 1 to 4.

TABLE 1

| Test Item | Positive or Negative Sample | Serum Sample ID | Luminescent signal intensity and negative/positive determination of the magnetic microspheres of Example 1 | Luminescent signal intensity and negative/positive determination of the magnetic microspheres of comparative Example 1 |
|---|---|---|---|---|
| CMV IgM | Negative | C336 | 5356 (Negative) | 105983 (Positive) |
| | | C128 | 1208 (Negative) | 62563 (Positive) |
| | | C500 | 4211 (Negative) | 8359 (Negative) |
| | | C228 | 1806 (Negative) | 5698 (Negative) |
| | | C86 | 2149 (Negative) | 7562 (Negative) |
| | | C471 | 2350 (Negative) | 2359 (Negative) |
| | | C60 | 4215 (Negative) | 10698 (Negative) |
| | | C348 | 1089 (Negative) | 2439 (Negative) |
| | | C502 | 4356 (Negative) | 5326 (Negative) |
| | | C377 | 6607 (Negative) | 7659 (Negative) |
| | Positive | CP1 | 159563 (Positive) | 165230 (Positive) |
| | | CP2 | 32859 (Positive) | 23597 (Positive) |
| | | CP3 | 60538 (Positive) | 53695 (Positive) |
| | | CP4 | 254714 (Positive) | 247796 (Positive) |
| | | CP5 | 114689 (Positive) | 120874 (Positive) |
| | | CP6 | 70899 (Positive) | 60899 (Positive) |
| | | CP7 | 240563 (Positive) | 257465 (Positive) |
| | | CP8 | 95686 (Positive) | 105693 (Positive) |
| | | CP9 | 95631 (Positive) | 75132 (Positive) |
| | | CP10 | 586044 (Positive) | 569212 (Positive) |

Note: Luminescent signal intensity is marked as positive when above 20,000 or negative when below 20,000. The same applies below.

TABLE 2

| Test Item | Positive or Negative Sample | Serum Sample ID | Luminescent signal intensity and negative/positive determination of the magnetic microspheres of Example 1 | Luminescent signal intensity and negative/positive determination of the magnetic microspheres of comparative Example 1 |
|---|---|---|---|---|
| TOXO IgG | Negative | C336 | 7546 (Negative) | 1168936 (Positive) |
| | | C348 | 5327 (Negative) | 5632 (Negative) |
| | | C389 | 2358 (Negative) | 905326 (Positive) |
| | | C323 | 4781 (Negative) | 5356 (Negative) |
| | | C369 | 5632 (Negative) | 153262 (Positive) |
| | | C350 | 8461 (Negative) | 50329 (Negative) |
| | | C377 | 2596 (Negative) | 268954 (Positive) |
| | | C86 | 5632 (Negative) | 7653 (Negative) |
| | | C60 | 2579 (Negative) | 4698 (Negative) |
| | | C102 | 5612 (Negative) | 7658 (Negative) |
| | Positive | TP1 | 286591 (Positive) | 295336 (Positive) |
| | | TP2 | 168354 (Positive) | 170562 (Positive) |
| | | TP3 | 105936 (Positive) | 98653 (Positive) |
| | | TP4 | 468992 (Positive) | 450879 (Positive) |
| | | TP5 | 56798 (Positive) | 50598 (Positive) |
| | | TP6 | 136587 (Positive) | 143287 (Positive) |
| | | TP7 | 154805 (Positive) | 168953 (Positive) |
| | | TP8 | 347761 (Positive) | 332567 (Positive) |
| | | TP9 | 269547 (Positive) | 254687 (Positive) |
| | | TP10 | 165392 (Positive) | 170589 (Positive) |

TABLE 3

| Test Item | Positive or Negative Sample | Serum Sample ID | Luminescent signal intensity and negative/positive determination of the magnetic microspheres of Example 1 | Luminescent signal intensity and negative/positive determination of the magnetic microspheres of comparative Example 1 |
|---|---|---|---|---|
| GAD65 | Negative | C336 | 5669 (Negative) | 496652 (Positive) |
| | | C348 | 3569 (Negative) | 3956 (Negative) |
| | | C369 | 7452 (Negative) | 6724 (Negative) |
| | | C323 | 4689 (Negative) | 8693 (Negative) |
| | | C377 | 3569 (Negative) | 2563 (Negative) |
| | | C321 | 5689 (Negative) | 6395 (Negative) |
| | | C350 | 4567 (Negative) | 7841 (Negative) |
| | | C60 | 5966 (Negative) | 3633 (Negative) |
| | | C471 | 5368 (Negative) | 5689 (Negative) |
| | | C500 | 2045 (Negative) | 196745 (Positive) |
| | Positive | GP1 | 40569 (Positive) | 36995 (Positive) |
| | | GP2 | 58611 (Positive) | 56321 (Positive) |
| | | GP3 | 106335 (Positive) | 86596 (Positive) |
| | | GP4 | 175986 (Positive) | 187642 (Positive) |
| | | GP5 | 40539 (Positive) | 46952 (Positive) |
| | | GP6 | 363571 (Positive) | 369882 (Positive) |
| | | GP7 | 140266 (Positive) | 132569 (Positive) |
| | | GP8 | 80563 (Positive) | 78536 (Positive) |
| | | GP9 | 253658 (Positive) | 265714 (Positive) |
| | | GP10 | 87420 (Positive) | 86536 (Positive) |

It can be seen from above Tables 1 to 3, TOXO antigen, GAD65 antigen, and CMV antigen coating the magnetic microspheres prepared according to Example 1 of the present disclosure demonstrated good binding ability with the corresponding antibody-positive samples, respectively, while presenting a completely negative signal for corresponding antibody-negative samples. This indicated that the magnetic microspheres prepared according to Example 1 disclosed herein had surface active groups with excellent binding ability with proteins, i.e., antigens. The binding of the surface active groups of the magnetic microspheres to the proteins was not affected at all by the polyacrylate polymers on the surface of the magnetic microspheres.

TABLE 4

| Test Item | Serum Sample ID | Luminescent signal intensity and negative/positive determination of the magnetic microspheres of Example 1 | Luminescent signal intensity and negative/positive determination of the magnetic microspheres of comparative Example 1 |
|---|---|---|---|
| TOXO IgG | C336 | 4284 (Negative) | 1224643 (Positive) |
| | C348 | 3999 (Negative) | 3792 (Negative) |
| | C389 | 2736 (Negative) | 824763 (Positive) |
| | C323 | 5742 (Negative) | 6224 (Negative) |
| | C369 | 4840 (Negative) | 123416 (Positive) |
| | C350 | 5631 (Negative) | 62498 (Positive) |
| | C377 | 3829 (Negative) | 243310 (Positive) |
| | C86 | 8763 (Negative) | 8511 (Negative) |
| | C60 | 6012 (Negative) | 5491 (Negative) |
| | C102 | 5843 (Negative) | 6161 (Negative) |
| GAD65 | C336 | 4464 (Negative) | 628768 (Positive) |
| | C348 | 3129 (Negative) | 2560 (Negative) |
| | C369 | 5412 (Negative) | 3072 (Negative) |
| | C323 | 3408 (Negative) | 103748 (Positive) |
| | C377 | 4012 (Negative) | 3178 (Negative) |
| | C321 | 3218 (Positive) | 3400 (Negative) |
| | C350 | 3520 (Negative) | 3078 (Negative) |
| | C60 | 1982 (Negative) | 2634 (Negative) |
| | C471 | 2561 (Negative) | 22766 (Positive) |
| | C500 | 2973 (Negative) | 201428 (Positive) |

TABLE 4-continued

| Test Item | Serum Sample ID | Luminescent signal intensity and negative/positive determination of the magnetic microspheres of Example 1 | Luminescent signal intensity and negative/positive determination of the magnetic microspheres of comparative Example 1 |
|---|---|---|---|
| CMV IgM | C336 | 2636 (Negative) | 133538 (Positive) |
| | C128 | 2715 (Negative) | 139161 (Positive) |
| | C500 | 5012 (Negative) | 5843 (Negative) |
| | C228 | 1892 (Negative) | 3584 (Negative) |
| | C86 | 2360 (Negative) | 4509 (Negative) |
| | C471 | 1743 (Negative) | 3764 (Negative) |
| | C60 | 3264 (Negative) | 202597 (Positive) |
| | C348 | 3464 (Negative) | 2676 (Negative) |
| | C502 | 1525 (Negative) | 2127 (Negative) |
| | C377 | 3672 (Negative) | 2085 (Negative) |

As indicated by Table 4, the magnetic microspheres prepared according to Example 1 disclosed herein had an obviously lower non-specific adsorption of antibodies in the samples than the non-specific adsorption of antibodies of the magnetic microsphere matrix in Comparative Example 1 that was not modified with the emulsion prepared as disclosed herein. In addition, for some special samples, Comparative Example 1 had falsely high test results which were not consistent with the clinical samples. The experiments and their data above has demonstrated that the magnetic microspheres in Example 1 disclosed herein have significant effects in reducing or avoiding non-specific protein adsorption.

Example 2

1) Preparation of Magnetic Microsphere Matrix

The magnetic microsphere matrix used in the present example was prepared according to the Chinese Patent Application Publication CN102746529A, especially Examples 1 to 6 thereof. That is, seed particles of polystyrene polymer were prepared, then modified with emulsion containing polyvinylpyrrolidone, divinylbenzene, styrene, and toluene (porogen), and subjected to emulsion polymerization to obtain porous polystyrene particles. The porous polystyrene particles were nitrified with nitric acid and incorporated with iron using $FeSO_4$. The resulting particles were coated and carboxyl functionalized to give the magnetic microsphere matrix with carboxyl functional groups used in the present example.

2) Preparation of Emulsion

The components of the emulsion and their percentages by weight were as follows:

| | |
|---|---|
| Hydroxyethyl methacrylate | 0.5%; |
| Neopentyl glycol dimethacrylate | 0.05%; |
| Ammonium persulfate | 0.2%; |
| Sodium dodecyl sulfonate, | 0.5%; and |
| Purified water | 98.75%. |

The above components were mixed according to their proportions, sonicated to fully dissolve the solid components, and further well mixed.

3) Preparation of Dispersion System

The magnetic microsphere matrix obtained from step 1) was dispersed in the emulsion prepared from step 2) at a concentration of 40 mg/mL, and sonicated for uniform dispersion of the magnetic microsphere matrix to obtain a dispersion system.

4) Polymerization Reaction and Post-Treatment

The dispersion system obtained from step 3) was stirred at 80° C. for 18 hours. The supernatant was removed by magnetic separation. The solids were washed 3 times with methanol and 5 times with water to give the magnetic microspheres.

5) Determination of Binding Performance of Surface Active Groups of Magnetic Microspheres The tests were performed similarly to the step 5) of Example 1, except that the magnetic microspheres used were replaced with the magnetic microspheres prepared in the step 4) of the present example. The results are shown in Tables 5-7.

6) Non-Specific Adsorption Test of Magnetic Microspheres

The tests were performed by repeating the step 6) of Example 1, except that the magnetic microspheres used were replaced with the magnetic microspheres prepared in the step 4) of the present example. The results are shown in Table 8.

Example 3

The experiment was carried out following the procedures of Example 2, except that the emulsion of Example 2 was replaced with the emulsion described below.

The components of the emulsion and their percentages by weight were as follows:

| | |
|---|---|
| Hydroxyethyl methacrylate | 0.5%; |
| Neopentyl glycol dimethacrylate | 0.2%; |
| Ammonium persulfate | 0.2%; |
| Sodium dodecyl sulfonate, | 0.5%; and |
| Purified water | 98.6%. |

The results are shown in Tables 5 to 8.

Comparative Example 2

The magnetic microsphere matrix was prepared according to the Chinese Patent Application Publication CN102746529A, especially Examples 1 to 4 thereof, and tested for the binding performance and non-specific adsorption of their surface active groups. The tests were performed in similar process and conditions according to the steps 5) and 6) of Example 2, except that the magnetic microsphere matrix used in the steps 5) and 6) of Example 2 were replaced with the magnetic microspheres prepared in the present example. The results are shown in Tables 5 to 8.

TABLE 5

| Test Item | Positive or Negative Sample | Serum Sample ID | Luminescent signal intensity and negative/positive determination of the magnetic microspheres of Example 2 | Luminescent signal intensity and negative/positive determination of the magnetic microspheres of Example 3 | Luminescent signal intensity and negative/positive determination of the magnetic microspheres of Comparative Example 2 |
|---|---|---|---|---|---|
| CMV IgM | Negative | C336 | 4728 (Negative) | 5044 (Negative) | 987762 (Positive) |
| | | C128 | 5689 (Negative) | 5682 (Negative) | 156942 (Positive) |
| | | C500 | 3529 (Negative) | 3768 (Negative) | 5782 (Negative) |
| | | C228 | 5430 (Negative) | 6048 (Negative) | 2634 (Negative) |
| | | C86 | 1945 (Negative) | 2044 (Negative) | 6851 (Negative) |
| | | C471 | 2356 (Negative) | 3086 (Negative) | 3654 (Negative) |
| | | C60 | 4879 (Negative) | 5047 (Negative) | 4810 (Negative) |
| | | C348 | 2561 (Negative) | 2758 (Negative) | 5730 (Negative) |
| | | C502 | 5873 (Negative) | 6048 (Negative) | 6820 (Negative) |
| | | C377 | 5126 (Negative) | 4985 (Negative) | 7873 (Negative) |
| | Positive | CP1 | 175642 (Positive) | 172484 (Positive) | 145637 (Positive) |
| | | CP2 | 43215 (Positive) | 49387 (Positive) | 26548 (Positive) |
| | | CP3 | 57863 (Positive) | 68240 (Positive) | 65487 (Positive) |
| | | CP4 | 234561 (Positive) | 234578 (Positive) | 235611 (Positive) |
| | | CP5 | 108431 (Positive) | 118524 (Positive) | 102453 (Positive) |
| | | CP6 | 894321 (Positive) | 824554 (Positive) | 785421 (Positive) |
| | | CP7 | 345210 (Positive) | 304117 (Positive) | 301245 (Positive) |
| | | CP8 | 86510 (Positive) | 86584 (Positive) | 98703 (Positive) |
| | | CP9 | 76431 (Positive) | 74438 (Positive) | 103241 (Positive) |
| | | CP10 | 421302 (Positive) | 440378 (Positive) | 486310 (Positive) |

TABLE 6

| Test Item | Positive or Negative Sample | Serum Sample ID | Luminescent signal intensity and negative/positive determination of the magnetic microspheres of Example 2 | Luminescent signal intensity and negative/positive determination of the magnetic microspheres of Example 3 | Luminescent signal intensity and negative/positive determination of the magnetic microspheres of Comparative Example 2 |
|---|---|---|---|---|---|
| TOXO IgG | Negative | C336 | 5412 (Negative) | 6685 (Negative) | 1251097 (Positive) |
| | | C348 | 5687 (Negative) | 5487 (Negative) | 6583 (Negative) |
| | | C389 | 3654 (Negative) | 1568 (Negative) | 897621 (Positive) |
| | | C323 | 4628 (Negative) | 5724 (Negative) | 4598 (Negative) |
| | | C369 | 5132 (Negative) | 5252 (Negative) | 168439 (Positive) |
| | | C350 | 2356 (Negative) | 4435 (Negative) | 19874 (Negative) |
| | | C377 | 3541 (Negative) | 2015 (Negative) | 284710 (Positive) |
| | | C86 | 6874 (Negative) | 7593 (Negative) | 8910 (Negative) |
| | | C60 | 3559 (Negative) | 3554 (Negative) | 5431 (Negative) |
| | | C102 | 6215 (Negative) | 6861 (Negative) | 7357 (Negative) |
| | Positive | TP1 | 275610 (Positive) | 245810 (Positive) | 259841 (Positive) |
| | | TP2 | 176354 (Positive) | 203357 (Positive) | 201684 (Positive) |
| | | TP3 | 96854 (Positive) | 95794 (Positive) | 102543 (Positive) |
| | | TP4 | 385672 (Positive) | 307972 (Positive) | 475689 (Positive) |
| | | TP5 | 46983 (Positive) | 52988 (Positive) | 49612 (Positive) |
| | | TP6 | 156432 (Positive) | 142583 (Positive) | 184256 (Positive) |
| | | TP7 | 179531 (Positive) | 205953 (Positive) | 135682 (Positive) |
| | | TP8 | 354613 (Positive) | 330610 (Positive) | 354621 (Positive) |
| | | TP9 | 254983 (Positive) | 304988 (Positive) | 201873 (Positive) |
| | | TP10 | 196543 (Positive) | 195579 (Positive) | 196826 (Positive) |

TABLE 7

| Test Item | Positive or Negative Sample | Serum Sample ID | Luminescent signal intensity and negative/positive determination of the magnetic microspheres of Example 2 | Luminescent signal intensity and negative/positive determination of the magnetic microspheres of Example 3 | Luminescent signal intensity and negative/positive determination of the magnetic microspheres of Comparative Example 2 |
|---|---|---|---|---|---|
| GAD65 | Negative | C336 | 5596 (Negative) | 4586 (Negative) | 516892 (Positive) |
| | | C348 | 3854 (Negative) | 4573 (Negative) | 4195 (Negative) |

TABLE 7-continued

| Test Item | Positive or Negative Sample | Serum Sample ID | Luminescent signal intensity and negative/positive determination of the magnetic microspheres of Example 2 | Luminescent signal intensity and negative/positive determination of the magnetic microspheres of Example 3 | Luminescent signal intensity and negative/positive determination of the magnetic microspheres of Comparative Example 2 |
|---|---|---|---|---|---|
| | | C369 | 7261 (Negative) | 6678 (Negative) | 5792 (Negative) |
| | | C323 | 4195 (Negative) | 4458 (Negative) | 7982 (Negative) |
| | | C377 | 2943 (Negative) | 3044 (Negative) | 3018 (Negative) |
| | | C321 | 6813 (Negative) | 8427 (Negative) | 5943 (Negative) |
| | | C350 | 5192 (Negative) | 6458 (Negative) | 8019 (Negative) |
| | | C60 | 5713 (Negative) | 4397 (Negative) | 3529 (Negative) |
| | | C471 | 4952 (Negative) | 5521 (Negative) | 4695 (Negative) |
| | | C500 | 2946 (Negative) | 3486 (Negative) | 186452 (Positive) |
| | Positive | GP1 | 50136 (Positive) | 82754 (Positive) | 49613 (Positive) |
| | | GP2 | 69842 (Positive) | 75864 (Positive) | 47621 (Positive) |
| | | GP3 | 163542 (Positive) | 182475 (Positive) | 98651 (Positive) |
| | | GP4 | 132549 (Positive) | 124458 (Positive) | 175626 (Positive) |
| | | GP5 | 50134 (Positive) | 66457 (Positive) | 56138 (Positive) |
| | | GP6 | 431562 (Positive) | 337581 (Positive) | 416235 (Positive) |
| | | GP7 | 150234 (Positive) | 204574 (Positive) | 153426 (Positive) |
| | | GP8 | 90125 (Positive) | 100254 (Positive) | 86423 (Positive) |
| | | GP9 | 176950 (Positive) | 186990 (Positive) | 214683 (Positive) |
| | | GP10 | 65432 (Positive) | 66784 (Positive) | 95634 (Positive) |

It can be seen from the above Table 5-7, TOXO antigen, GAD65 antigen, and CMV antigen coating the magnetic microspheres prepared according to Examples 2 and 3 of the present disclosure demonstrated good binding ability with the corresponding antibody-positive samples, respectively, while presenting a completely negative signal for corresponding antibody-negative samples. This indicated that the magnetic microspheres prepared according to Examples 2 and 3 disclosed herein had surface active groups with excellent binding ability with proteins, i.e., antigens. The binding of the surface active groups of the magnetic microspheres to the proteins was not affected at all by the polyacrylate polymers on the surface of the magnetic microspheres.

TABLE 8

| Test Item | Serum Sample ID | Luminescent signal intensity and negative/positive determination of the magnetic microspheres of Example 2 | Luminescent signal intensity and negative/positive determination of the magnetic microspheres of Example 3 | Luminescent signal intensity and negative/positive determination of the magnetic microspheres of comparative Example 2 |
|---|---|---|---|---|
| TOXO IgG | C336 | 5613 (Negative) | 6717 (Negative) | 135649 (Positive) |
| | C348 | 4201 (Negative) | 4254 (Negative) | 6739 (Negative) |
| | C389 | 3265 (Negative) | 3858 (Negative) | 984352 (Positive) |
| | C323 | 4952 (Negative) | 5554 (Negative) | 7762 (Negative) |
| | C369 | 5169 (Negative) | 4867 (Negative) | 163852 (Positive) |
| | C350 | 4821 (Negative) | 2021 (Negative) | 59613 (Positive) |
| | C377 | 2956 (Negative) | 3467 (Negative) | 34162 (Positive) |
| | C86 | 9543 (Negative) | 10420 (Negative) | 6591 (Negative) |
| | C60 | 6830 (Negative) | 7240 (Negative) | 6135 (Negative) |
| | C102 | 2465 (Negative) | 1867 (Negative) | 4261 (Negative) |
| GAD65 | C336 | 5913 (Negative) | 6785 (Negative) | 694351 (Positive) |
| | C348 | 4256 (Negative) | 4572 (Negative) | 6521 (Negative) |
| | C369 | 6289 (Negative) | 4420 (Negative) | 2564 (Negative) |
| | C323 | 6205 (Negative) | 5796 (Negative) | 4694 (Negative) |
| | C377 | 6031 (Negative) | 6457 (Negative) | 6191 (Negative) |
| | C321 | 4316 (Negative) | 4358 (Negative) | 4603 (Negative) |
| | C350 | 2546 (Negative) | 2781 (Negative) | 6405 (Negative) |
| | C60 | 3194 (Negative) | 3368 (Negative) | 2019 (Negative) |
| | C471 | 2468 (Negative) | 2941 (Negative) | 3461 (Negative) |
| | C500 | 4619 (Negative) | 5501 (Negative) | 235874 (Positive) |
| CMV IgM | C336 | 3491 (Negative) | 3934 (Negative) | 191635 (Positive) |
| | C128 | 6159 (Negative) | 6679 (Negative) | 124671 (Positive) |
| | C500 | 3461 (Negative) | 3587 (Negative) | 3054 (Negative) |
| | C228 | 2016 (Negative) | 2847 (Negative) | 4916 (Negative) |
| | C86 | 3469 (Negative) | 4013 (Negative) | 2046 (Negative) |
| | C471 | 1954 (Negative) | 2428 (Negative) | 4671 (Negative) |
| | C60 | 5068 (Negative) | 244618 (Positive) | 2749 (Negative) |

TABLE 8-continued

| Test Item | Serum Sample ID | Luminescent signal intensity and negative/positive determination of the magnetic microspheres of Example 2 | Luminescent signal intensity and negative/positive determination of the magnetic microspheres of Example 3 | Luminescent signal intensity and negative/positive determination of the magnetic microspheres of comparative Example 2 |
|---|---|---|---|---|
| | C348 | 5319 (Negative) | 5679 (Negative) | 6942 Negative) |
| | C502 | 1605 (Negative) | 1785 (Negative) | 3491 (Negative) |
| | C377 | 3259 (Negative) | 4840 (Negative) | 5192 (Negative) |

It can be seen from Table 8, the magnetic microspheres prepared according to Examples 2 and 3 disclosed herein had a non-specific adsorption of antibodies in the samples that was obviously lower than that of the magnetic microsphere matrix in Comparative Example 2 which was not modified with the emulsion prepared as disclosed herein. In addition, for some special samples, Comparative Example 2 had falsely high test results which were not consistent with the clinical samples. The experiments and data above had demonstrated that the magnetic microspheres in Examples 2 and 3 disclosed herein had significant effects in reducing or avoiding non-specific protein adsorption.

Example 4

1) Preparation of Magnetic Microsphere Matrix

The magnetic microsphere matrix used in the present example was prepared according to the Chinese Patent Application Publication CN102746529A, especially Examples 1 to 6 thereof.

2) Preparation of Emulsion

The components of the emulsion and their percentages by weight were as follows:

| | |
|---|---|
| Butyl methacrylate | 10%; |
| 1,6-hexanediol dimethacrylate | 2%; |
| Potassium persulfate | 1%; |
| Sodium dodecyl sulfate | 0.5%; and |
| Water | 86.5%. |

The above components were mixed according to their proportions, sonicated to fully dissolve the solid components, and emulsified in a high-shear emulsifying machine for 20 minutes.

3) Preparation of Dispersion System

The magnetic microsphere matrix obtained from step 1) was dispersed in the emulsion prepared from step 2) at a concentration of 50 mg/mL, and sonicated for uniform dispersion of the magnetic microsphere matrix to obtain a dispersion system.

4) Polymerization Reaction and Post-Treatment

The dispersion system obtained from step 3) was stirred at 75° C. for 28 hours. The supernatant was removed by magnetic separation. The solids were washed 3 times with methanol and 5 times with water to give the magnetic microspheres.

5) Determination of Binding Performance of Surface Active Groups of Magnetic Microspheres The tests were performed similarly to the step 5) of Example 1, except that the magnetic microspheres used were replaced with the magnetic microspheres prepared in the step 4) of the present example.

It can be seen from the experimental data (not listed here) that the active groups of magnetic microspheres had similar binding capacity with antigen proteins with those prepared in Examples 1 and 2. Antigens coating the magnetic microspheres were excellently binded with the antibodies in the sample, while presenting a completely negative signal in the negative samples.

6) Non-Specific Adsorption Test of Magnetic Microspheres

The tests were performed by repeating the step 6) of Example 1, except that the magnetic microspheres used were replaced with the magnetic microspheres prepared in the step 4) of the present example.

It can be seen from the experimental data (not listed here) that, similar as those in Example 1 and 2, the antigen-coated magnetic microspheres prepared according to the present example had little non-specific adsorption in an adsorption test.

Example 5

1) Preparation of Magnetic Microsphere Matrix

The magnetic microsphere matrix used in the present example was prepared according to the Chinese Patent Application Publication CN102746529A, especially Examples 1 to 4 thereof.

2) Preparation of Emulsion

The components of the emulsion and their percentages by weight were as follows:

| | |
|---|---|
| Ethyl methacrylate | 10%; |
| 1,3-propanediol dimethacrylate | 2%; |
| Ammonium persulfate | 1%; |
| N-decyl sulfate | 0.5%; and |
| Water | 86.5%. |

The above components were mixed according to their proportions, sonicated to fully dissolve the solid components, and homogenized a high-pressure homogenizer for 20 minutes.

3) Preparation of Dispersion System

The magnetic microsphere matrix obtained from step 1) was dispersed in the emulsion prepared from step 2) at a concentration of 50 mg/mL, and sonicated for uniform dispersion of the magnetic microsphere matrix to obtain a dispersion system.

4) Polymerization Reaction and Post-Treatment

The dispersion system obtained from step 3) was stirred at 70° C. for 24 hours. The supernatant was removed by magnetic separation. The solids were washed 3 times with methanol and 5 times with water to give the magnetic microspheres.

5) Determination of Binding Performance of Surface Active Groups of Magnetic Microspheres The tests were performed similarly to the step 5) of Example 1, except that the magnetic microspheres used were replaced with the magnetic microspheres prepared in the step 4) of the present example.

It can be seen from the experimental data (not listed here) that the active groups of magnetic microspheres had similar binding capacity with antigen proteins with those prepared in Examples 1 and 2. Antigens coating the magnetic microspheres were excellently binded with the antibodies in the sample, while presenting a completely negative signal in the negative samples.

6) Non-Specific Adsorption Test of Magnetic Microspheres

The tests were performed by repeating the step 6) of Example 1, except that the magnetic microspheres used were replaced with the magnetic microspheres prepared in the step 4) of the present example.

It can be seen from the experimental data (not listed here) that, similar as those in Example 1 and 2 the antigen-coated magnetic microspheres prepared according to the present example had little non-specific adsorption in an adsorption test.

Example 6

1) Preparation of Magnetic Microsphere Matrix

The magnetic microsphere matrix used in the present example was prepared according to the Chinese Patent Application Publication CN102746529A, especially Examples 1 to 4 thereof.

2) Preparation of Emulsion

The components of the emulsion and their percentages by weight were as follows:

| | |
|---|---|
| Hydroxypropyl methacrylate | 12%; |
| 1,3-propanediol dimethacrylate | 2%; |
| Sodium persulfate | 1%; |
| Sodium dodecyl sulfate | 0.5%; and |
| Water | 84.5%. |

The above components were mixed according to their proportions, sonicated to fully dissolve the solid components, and emulsified in a high-shear emulsifying machine for 20 minutes.

3) Preparation of Dispersion System

The magnetic microsphere matrix obtained from step 1) was dispersed in the emulsion prepared from step 2) at a concentration of 100 mg/mL, and sonicated for uniform dispersion of the magnetic microsphere matrix to obtain a dispersion system.

4) Polymerization Reaction and Post-Treatment

The dispersion system obtained from step 3) was stirred at 70° C. for 20 hours. The supernatant was removed by magnetic separation. The solids were washed 3 times with ethanol and 5 times with water to give the magnetic microspheres.

5) Determination of Binding Performance of Surface Active Groups of Magnetic Microspheres The tests were performed similarly to the step 5) of Example 1, except that the magnetic microspheres used were replaced with the magnetic microspheres prepared in the step 4) of the present example.

It can be seen from the experimental data (not listed here) that the active groups of magnetic microspheres have similar binding capacity with antigen proteins as those prepared in Example 1 and 2. Antigens coating the magnetic microspheres were excellently binded with the antibodies in the sample, while presenting a completely negative signal in the negative samples.

6) Non-Specific Adsorption Test of Magnetic Microspheres

The tests were performed by repeating the step 6) of Example 1, except that the magnetic microspheres used were replaced with the magnetic microspheres prepared in the step 4) of the present example. It can be seen from the experimental data (not listed here) that, similar as those in Examples 1 and 2, the antigen-coated magnetic microspheres prepared according to the present example had little non-specific adsorption in an adsorption test.

The description above has provided specific details of the present disclosure. However, a person skilled in the art can readily appreciate modifications of the embodiments disclosed herein without deviating from the spirit and scope of the present disclosure. It should also be noted that the respective aspects, various components of different embodiments, and numerous technical features recited herein can be in combined or interchanged in part or in whole. In the embodiment above, each particular embodiment referring to another can be suitably combined with any other embodiments, which could be appreciated by a person skilled in the art. Finally, a person skilled in the art can comprehend that the description above is only for the purpose of illustration by way of example, without limiting the present disclosure in any aspect.

The invention claimed is:
1. A method for preparing a magnetic microsphere for separation of biological protein, characterized in that it comprises:

a. preparing an emulsion;
b. dispersing a magnetic microsphere matrix with magnetism into the emulsion to generate a dispersion system; and
c. subjecting the dispersion to a polymerization reaction; wherein the magnetic microsphere matrix is a magnetic particle modified with an active group on surface thereof; further wherein the active group is at least one selected from the group consisting of: a carboxyl group and a sulfonic acid group;
and
wherein the emulsion comprises the following components: an acrylic monoester compound selected from the group consisting of methyl methacrylate, ethyl methacrylate, hydroxyethyl methacrylate, n-propyl methacrylate, hydroxypropyl methacrylate, n-butyl methacrylate, and hydroxybutyl methacrylate; an acrylic diol ester compound selected from the group consisting of glycol dimethacrylate, 1,3-propanediol dimethacrylate, 1,3-butanediol dimethacrylate, 1,4-butanediol dimethacrylate, neopentyl glycol dimethacrylate and 1,6-hexanediol dimethacrylate; an anionic surfactant selected from the group consisting of sodium dodecyl sulfate, sodium dodecyl sulfonate, sodium hexadecyl sulfonate, and sodium n-decyl sulfate; water; and a water-soluble initiator selected from the group consisting of sodium persulfate, potassium persulfate, and ammonium persulfate.

2. The method of claim 1, characterized in that the emulsion comprises 0.5 to 30 wt % of the acrylic monoester compound, 0.05 to 5 wt % of the acrylic diol ester compound, 0.2 to 2 wt % of the water-soluble initiator, 0.1 to 1 wt % of the anionic surfactant, and 62 to 99 wt % of water, based on the total weight of the emulsion.

3. The method of claim 1, characterized in that the weight content of the acrylic diol ester compound is 5 to 15% of the weight content of the acrylic monoester compound.

4. The method of claim 3, characterized in that the weight content of the acrylic diol ester compound is 10% of the weight content of the acrylic monoester compound.

5. The method of claim 1, characterized in that the active group is capable of bonding with a biological protein.

6. The method of claim 1, characterized in that the particle size of the magnetic microsphere matrix is 0.1 to 5 µm.

7. The method of claim 1, characterized in that the magnetic microsphere matrix in the dispersion system has a concentration of 10 to 150 mg/m L.

8. The method of claim 7, characterized in that the polymerization reaction in the step c is performed under a temperature of 60 to 90° C. with a reaction time of 10-40 h.

9. The method of claim 1, characterized in that in the step a, the emulsion is prepared by mixing together the components of the emulsion uniformly; and
the method further comprises a step d following the step c: performing a solid-liquid separation with the product of the step c and washing solid matter obtained therefrom to generate the magnetic microsphere; wherein the solid-liquid separation in the step d is performed by magnetic separation or centrifugation, the washing is performed for a plurality of times with organic solvent and water in sequence, and the organic solvent is one or more selected from the group consisting of alcohol, ester, and halogenated hydrocarbon.

10. The method of claim 1, wherein the active group is a carboxyl group.

11. The method of claim 1, wherein the acrylic monoester compound is methyl methacrylate.

12. The method of claim 1, wherein the acrylic diol ester is glycol dimethacrylate.

* * * * *